United States Patent [19]

Garabedian

[11] Patent Number: Plant 5,903

[45] Date of Patent: Mar. 17, 1987

[54] PLUM TREE "GAR JUMBO"

[76] Inventor: John M. Garabedian, 3104 E. Huntington Blvd., Fresno, Calif. 93702

[21] Appl. No.: 766,446

[22] Filed: Aug. 19, 1985

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is somewhat similar to the Autumn Rosa Plum Tree (patented), concurrently with which it bears fruit, but which is distinguished therefrom characteristically by producing fruit which is larger in size, deeper and fuller in external color, and possesses a substantially heavier bloom.

1 Drawing Figure

BACKGROUND OF THE NEW VARIETY

The present invention relates to a new and distinct variety of plum tree, which has been denominated varietally as "Gar Jumbo", and which is broadly similar to the Autumn Rosa Plum Tree (patented), of which it is most closely similar, but from which it is distinguished therefrom in bearing fruit which is larger in size, deeper and richer in skin color, and having a heavier bloom.

The new variety is broadly characterized by bearing fruit that is most similar to the Autumn Rosa Plum Tree (patented) with which it ripens at approximately the same time, but from which it is distinguished therefrom by producing a plum which is significantly larger than the plum produced by the "Autumn Rosa" tree.

In an effort to upgrade his fruit products, the applicant is continuously on the alert to locate new varieties that might appear as sports or mutations on the fruit trees of any of his several farms. In the development of new and distinct varieties of plums, the applicant has germinated and grown thousands of randomly pollinated seedlings to maturity, and evaluated the resultant trees and their fruit. The subject variety is a result of his efforts in germinating the aforementioned seedlings.

The plum tree of the present invention is noteworthy for the larger fruit that is produced, the deeper skin color, and the significantly heavier bloom, than that produced by the "Autumn Rosa" variety.

ORIGIN

The present variety of plum tree was a seedling of unknown parentage grown in the seedling nursery at the inventor's ranch located at Kings Canyon Road and Fowler Avenue, Fresno, County of Fresno, State of California, in 1977. The seedling was observed for several years prior to recognition of its desirable characteristics. The applicant asexually reproduced the subject plum by budding the new and distinct variety to seedling trees which were planted at the applicant's orchard designated as Ranch No. 3, located at Belmont Avenue, Fresno, County of Fresno, State of California. This first asexual reproduction was performed in 1981. The resultant progeny were found to possess the same distinctive characteristics as the original seedling.

BRIEF DESCRIPTION OF THE DRAWING

The accompanying drawing is a color photograph of a characteristic twig bearing typical leaves, two plums are shown displaying their external coloration, one of such plums having the bloom removed to show the distinct coloration at maturity, a plum is halved transversely of the suture plane to illustrate the flesh coloration and stone characteristics of the subject variety.

DETAILED DESCRIPTION

Referring more specifically to the pomological details of this new and distinct variety of plum tree, the following has been observed under the ecological conditions prevailing in the designated orchards in Fresno, Calif. All major color code identifications are by reference to the Munsell Limit Color Cascade, although some common color names are used occasionally.

TREE

Size: Medium to large.
Vigor: Vigorous.
Figure: Upright, spreading, dense, vase-formed.
Productivity: Productive to very productive.
Regularity of bearing: Regular.
Trunk:
- *Thickness.*—Medium.
- *Texture of bark.*—Medium.

Branches:
- *Thickness.*—Medium.
- *Texture.*—Medium.
- *Color.*—Brown, (MCC 28-13), with broad, lighter colored striations.
- *Lenticels.*—Average in number, medium in size.

LEAVES

Shoot:
- *Size.*—Medium.
- *Length.*—10.27±0.86 cm.
- *Width.*—4.23±0.39 cm.
- *Form.*—Slightly obovate, acuminate, pointed.
- *Thickness.*—Medium.
- *Color.*—Dark Green, upper surface (MCC 16-14 to 17-14); lower surface somewhat lighter and grayer.
- *Texture.*—Nearly smooth.
- *Marginal form.*—Crenate.
- *Petiole.*—length — medium; Thickness — medium to slender.
- *Glands.*—Average number — variable; in a range from 0 to 3; very small in size; mixed in shape, green in color; positioned at the base of the blade.

*Stipules.*—Linear and persistent.

Spur:

*Size.*—Small to medium.

*Length.*—8.83±1.74 cm.

*Width.*—3.04±0.40 cm.

*Form.*—Narrowly oval to slightly obovate, acuminate, the base being long and acuminate, pointed.

*Thickness.*—Medium.

*Color.*—Similar to Spur, noted above.

*Texture.*—Nearly smooth.

*Marginal form.*—Crenate.

*Petiole.*—Short to medium long.

*Glands.*—Completely lacking in the Spur.

Flower buds: Small, short, plump, free and glabrous.

Flowers: Medium in size, white.

*Date of first bloom.*—Feb. 17, 1984.

*Date of full bloom.*—Mar. 3, 1984; an early bloom as compared to other varieties.

FRUIT

Maturity when described: Ripe for eating; August 8.

Size: Uniform in size; large to very large.

*Axial diameter.*—5.81±0.37 cm.

*Diameter transverse in suture plane.*—6.20±0.16 cm.

*Diameter transverse in cheek plane.*—5.97±0.36 cm.

Form: Uniform symmetrical, globose.

Suture: An inconspicuous, very shallow groove extending from the base to the apex; there is a slight depression beyond the pistil point.

Ventral surface: Very slightly rounded and lipped throughout; lips are equal; ventral surface is generally longer than the dorsal surface.

Cavity: Rounded and nearly circular; the suture appears on one side; the cavity depth is 0.87±0.23 cm., the cavity breadth is 1.99±0.26 cm.; markings — none.

Base: Rounded to slightly truncated.

Apex: Rounded.

Pistil point: Oblique.

Stem:

*Length.*—Medium long; length 1.75 cm.

*Thickness.*—Moderately stout.

Skin: Medium thickness; medium texture; slightly bitter; tenacious to flesh; no observed tendency to crack.

Color: Medium Red where located in a shaded area, (MCC 37-14); very Dark Maroon to Mahogony Red in other areas, (MCC 35-16).

Bloom color: Blue-Gray (MCC 1-5 to 1-6).

Dots: Inconspicuous under the heavy bloom with bloom removed: small, Light Brown, usually numerous apically, less frequent or completely missing on one or both cheeks, completely absent at shoulders and in the cavity of the stem.

Flesh:

*Color.*—Light Yellow (MCC 28-3), with very slight reddish tinge apically.

*Surface of the pit cavity.*—Somewhat darker Yellow than the flesh color, indicated above.

*Fibers.*—Few and fine.

*Ripening.*—Even.

*Amygdalin.*—Wanting.

*Texture.*—Medium to firm; fine; meaty.

*Juice.*—Scant.

*Flavor.*—Mild.

*Aroma.*—Wanting.

*Eating quality.*—Good.

Stone: Semi-free.

*Size.*—Medium to large.

*Length.*—2.29±0.17 cm.

*Breadth.*—1.95±0.14 cm.

*Thickness.*—1.14±0.06 cm.

*Form.*—Oval, to broad oval.

*Base.*—Straight.

*Hilum.*—Narrow, oblong.

*Apex.*—Acuminate.

*Sides.*—Nearly equal.

*Surface.*—Rugose; ridges jagged, toward the base to the apex.

*Ventral edge.*—Thin; without wing throughout.

*Dorsal edge.*—Narrow with a deep, broad groove, positioned toward the base, to above the center.

*Ridges.*—Continuous.

*Color of stone.*—Light Brown (MCC 32-1).

*Tendency to split.*—Slight.

Use: Market, local and dessert.

Keeping quality: Good.

Resistance to insects.—Medium.

Resistance to disease: Medium.

Shipping quality: Good.

Although the new variety of plum tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, I claim:

1. A new and distinct variety of plum tree substantially as illustrated and described which is somewhat similar to the Autumn Rosa Plum Tree (patented), with which it bears fruit which matures at substantially the same time, but from which it is distinguished therefrom by bearing fruit of a larger size, having a skin color which is a deeper, darker Maroon, and having a heavier bloom.

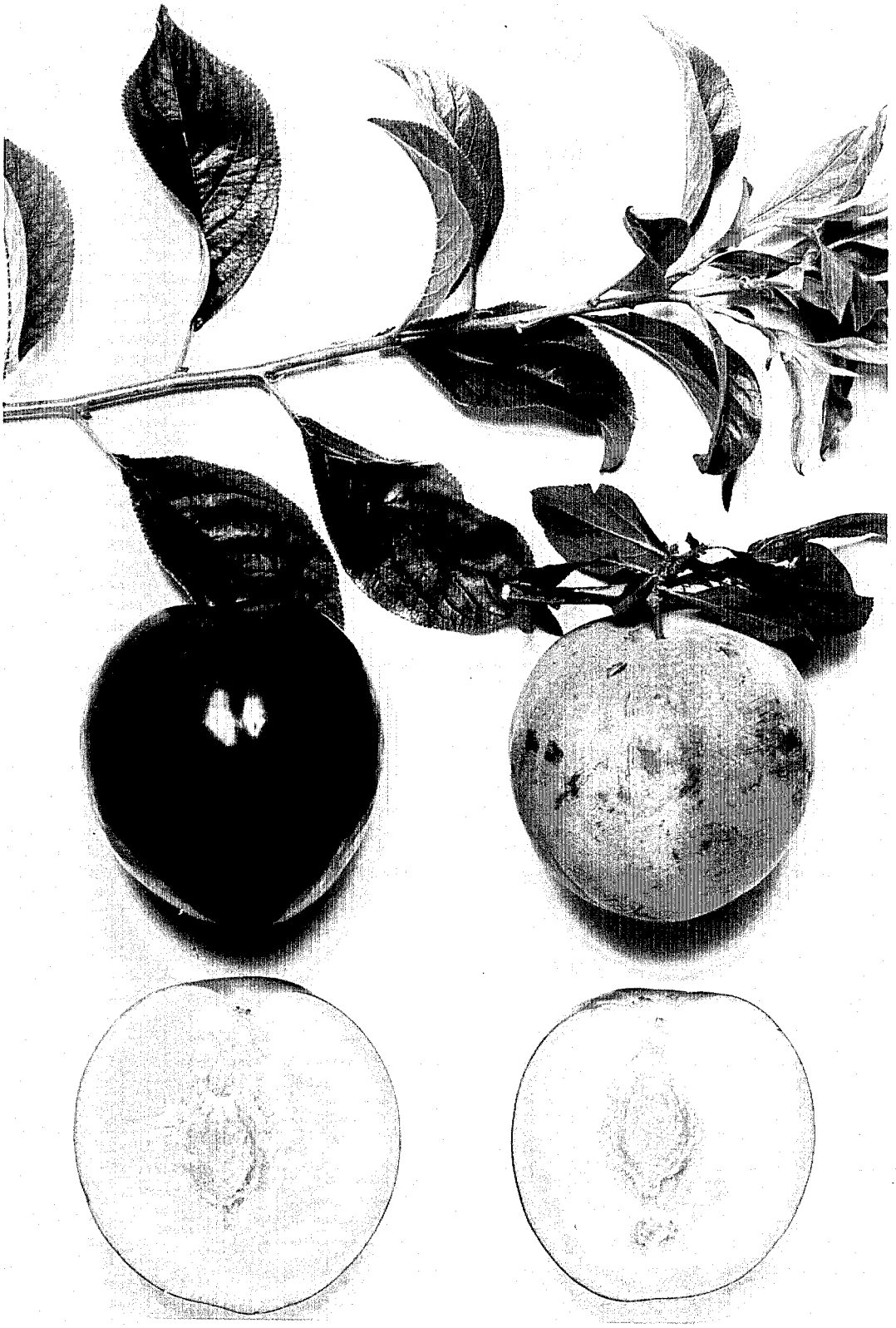

* * * * *